(12) United States Patent
Suzuki

(10) Patent No.: US 8,846,318 B2
(45) Date of Patent: *Sep. 30, 2014

(54) METHOD FOR IDENTIFYING OLFACTORY RECEPTOR INCLUDED IN ONE OLFACTORY CELL

(71) Applicant: Panasonic Corporation, Osaka (JP)

(72) Inventor: Masato Suzuki, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,759

(22) Filed: Mar. 22, 2013

(65) Prior Publication Data

US 2013/0273539 A1 Oct. 17, 2013

(30) Foreign Application Priority Data

Apr. 17, 2012 (JP) ................................. 2012-093603

(51) Int. Cl.
*C12Q 1/68* (2006.01)
*C07H 21/04* (2006.01)

(52) U.S. Cl.
CPC ............ *C12Q 1/6881* (2013.01); *C12Q 1/6876* (2013.01)
USPC ........................ 435/6.12; 435/6.17; 536/24.33

(58) Field of Classification Search
CPC ..... C12Q 1/6881; C12Q 1/6876; C07H 21/04
USPC ............................. 435/6.12, 6.17; 536/24.33
See application file for complete search history.

(56) References Cited

U.S. PATENT DOCUMENTS 7,344,845 B2   3/2008   Han et al.

OTHER PUBLICATIONS

Genbank Accession No. AY317748—*Mus musculus* olfactory receptor Olfr67 (Olfr67) gene, complete cds (GI: 32057272, submitted by Sanders et al. Jun. 6, 2003, retrieved on Mar. 16, 2014 from http://www.ncbi.nlm.nih.gov/nuccore/AY3177498).*
Genbank Accession No. X92969—*Mus musculus* OR23 gene (GI: 1419015, submitted by Tsuboi et al. Nov. 13, 1995, retrieved on Mar. 23, 2014 from http://www.ncbi.nlm.nih.gov/nuccore/ X92969).*
Touhara K, Sengoku S, Inaki K, Tsuboi A, Hirono J, Sato T, Sakano H, Haga T. Functional identification and reconstitution of an odorant receptor in single olfactory neurons. Proc Natl Acad Sci U S A. Mar. 30, 1999; 96(7):4040-5.*
Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*
Rouquier S, Friedman C, Delettre C, van den Engh G, Blancher A, Crouau-Roy B, Trask BJ, Giorgi D. A gene recently inactivated in human defines a new olfactory receptor family in mammals. Hum Mol Genet. Sep. 1998; 7(9):1337-45.*
Rouquier S, Blancher A, Giorgi D. The olfactory receptor gene repertoire in primates and mouse: evidence for reduction of the functional fraction in primates. Proc Natl Acad Sci U S A. Mar. 14, 2000; 97(6):2870-4.*
Rouquier S, Stubbs L, Gaillard-Sanchez I, Giorgi D. Sequence and chromosomal localization of the mouse ortholog of the human olfactory receptor gene 912-93. Mamm Genome. Dec. 1999; 10(12):1172-4.*
Young JM, Trask BJ. (2002A) The sense of smell: genomics of vertebrate odorant receptors. Hum Mol Genet. May 15, 2002; 11(10):1153-60. Review.*
Otaki JM, Yamamoto H, Firestein S. Odorant receptor expression in the mouse cerebral cortex. J Neurobiol. Feb. 15, 2004; 58(3):315-27.*
Young et al. (2002B). Different evolutionary processes shaped the mouse and human olfactory receptor gene families. Hum Mol Genet. Mar. 1, 2002;11(5):535-46.*
Parmentier M, Libert F, Schurmans S, Schiffmann S, Lefort A, Eggerickx D, Ledent C, Mollereau C, Gérard C, Perret J, et al. Expression of members of the putative olfactory receptor gene family in mammalian germ cells. Nature. Jan. 30, 1992; 355(6359):453-5.*
Zhang X, Firestein S. The olfactory receptor gene superfamily of the mouse. Nat Neurosci. Feb. 2002; 5(2):124-33.*
Bettina Malnic, Junzo Hirono, Takaaki Sato and Linda B. Buck, "Combinatorial Receptor Codes for Odors" Cell, vol. 96, 713-723, Mar. 5, 1999, Cell Press.
Touhara K., Sengoku S., Inaki K., Tsuboi A., Hirono J., Sato T., Sakano H., and Haga T., "Functional identification and reconstitution of an odorant receptor in single olfactory neurons", Proc. Natl. Acad. Sci. USA, vol. 96, 4040-4045, Mar. 1999.
Hamana H., Hirono J., Kizumi M. and Sato T., "Sensitivity-dependent Hierarchical Receptor Codes for Odors" Chem. Senses 28 (2): 87-104, 2003, Oxford University Press Retrieved from Internet <http://chemes.oxfordjournals.org/>.
Non-final office action of U.S. Appl. No. 13/784,518 issued on Apr. 8, 2014.
Zhang et al. The olfactory reporter gene superfamily of the mouse, Nature Neuroscience (2002) vol. 5, No. 2, pp. 124-133.
Lowe et al. A computer program for selection of oligonucleotide primers for polymerase chain reactions, Necleic Acids Res. (1990) vol. 18, No. 7,pp. 1757-1761.

* cited by examiner

*Primary Examiner* — Angela M Bertagna
*Assistant Examiner* — Olayinka Oyeyemi
(74) *Attorney, Agent, or Firm* — Panasonic Patent Center

(57) ABSTRACT

The present invention provides a novel method for identifying an olfactory receptor included in one olfactory cell. In the present invention, amplified is the cDNA derived from the mRNA of the one olfactory cell by a PCR method using a forward primer represented by SEQ ID: 01 and a reverse primer represented by SEQ ID: 02. Subsequently, determined is whether or not a gene sequence of the amplified cDNA corresponds with one gene sequence included in gene sequences coding for olfactory receptors included in the mouse olfactory receptor group A. Finally, determined is that the olfactory receptor included in the one olfactory cell is the olfactory receptor which corresponds to the one gene sequence which corresponds with the gene sequence of the cDNA in the previous step, if the gene sequence of the cDNA corresponds with the one gene sequence in the previous step.

4 Claims, 7 Drawing Sheets

1: Comparative example 1
2: Comparative example 2
3: Comparative example 3
4: Example 1

SEQ ID: 03
G (guanine) -C (cytosine) -I (inosine) -T (thymine) -A (adenine) -Y (thymine or cytosine) -G (guanine) -A (adenine) -Y (thymine or cytosine) -C (cytosine) -G (guanine) -I (inosine) -T (thymine) -A (adenine) -Y (thymine or cytosine) -G (guanine) -T (thymine) -I (inosine) -G (guanine) -C (cytosine) -I (inosine) -A (adenine) -T (thymine) -I (inosine) -T (thymine) -G (guanine)

SEQ ID: 04
T (thymine) -C (cytosine) -Y (thymine or cytosine) -T (thymine) -T (thymine) -R (guanine or adenine) -T (thymine) -T (thymine) -I (inosine) -C (cytosine) -K (guanine or thymine) -I (inosine) -A (adenine) -G (guanine) -I (inosine) -G (guanine) -W (adenine or thymine) -R (guanine or adenine) -T (thymine) -A (adenine) -I (inosine) -A (adenine) -Y (thymine or cytosine) -I (inosine) -A (adenine) -S (guanine or cytosine) -I (inosine) -G (guanine) -G (guanine) -R (guanine or adenine) -T (thymine) -T (thymine)

SEQ ID: 05
T (thymine) -C (cytosine) -I (inosine) -T (thymine) -S (guanine or cytosine) -R (guanine or adenine) -T (thymine) -T (thymine) -I (inosine) -C (cytosine) -K (guanine or thymine) -I (inosine) -A (adenine) -R (guanine or adenine) -I (inosine) -S (guanine or cytosine) -A (adenine) -R (guanine or adenine) -T (thymine) -A (adenine) -I (inosine) -A (adenine) -T (thymine) -I (inosine) -A (adenine) -T (thymine) -I (inosine) -G (guanine) -G (guanine) -R (guanine or adenine) -T (thymine) -T (thymine)

SEQ ID: 06
R (guanine or adenine) -T (thymine) -T (thymine) -I (inosine) -C (cytosine) -K (guanine or thymine) -I (inosine) -A (adenine) -R (guanine or adenine) -I (inosine) -S (guanine or cytosine) -W (adenine or thymine) -R (guanine or adenine) -T (thymine) -A (adenine) -I (inosine) -A (adenine) -T (thymine) -R (guanine or adenine) -A (adenine) -A (adenine) -I (inosine) -G (guanine) -G (guanine) -R (guanine or adenine) -T (thymine) -T (thymine)

Fig. 5

SEQ ID: 07
A (adenine) -T (thymine) -G (guanine) -G (guanine) -C (cytosine) -I (inosine) -T (thymine) -A (adenine) -Y (thymine or cytosine) -G (guanine) -A (adenine) -Y (thymine or cytosine) - M (adenine or cytosine) -G (guanine) -I (inosine) -T (thymine) - A (adenine) -Y (thymine or cytosine) -G (guanine) -T (thymine) -I (inosine) -G (guanine) -C (cytosine)

SEQ ID: 08
A (adenine) -T (thymine) -R (guanine or adenine) -A (adenine) - A (adenine) -I (inosine) -G (guanine) -G (guanine) -R (guanine or adenine) -T (thymine) -T (thymine) -I (inosine) -A (adenine) -R (guanine or adenine) -C (cytosine) -A (adenine) -T (thymine) -I (inosine) -G (guanine) -G (guanine)

SEQ ID: 09
A (adenine) -C (cytosine) -I (inosine) -A (adenine) -C (cytosine) - I (inosine) -G (guanine) -A (adenine) -I (inosine) -A (adenine) -G (guanine) -R (guanine or adenine) -T (thymine) -G (guanine) -I (inosine) -G (guanine) -A (adenine) -I (inosine) -S (guanine or cytosine) -C (cytosine) -R (guanine or adenine) -C (cytosine) -A (adenine) -I (inosine) -G (guanine) -T (thymine)

Fig. 6

SEQ ID: 10
TTGCTTGGTCTTGACGCCATAGATGATGGGGTTAAGCATTGG
GGGCACCACCACATAGAGGTTGGCCACTAGGATGTGGATGTG
GCGAGGAACTGTTTTGCCTCCAAAGCGATGGGCAAAAAATGA
AAAGAATGCAGGAGTGTAGAATAAAAGAATAACACAGATGTG
GGAGCCACATGTGTTGAGGGCCTTGTATCTGGCAGCCCAGGA
AGGGATTTGAAAAACAGTGCGAAGAATCATGGTGTAGGAAAT
AATGATGAGTAGTATCTAGCCTAGTAGACAGGAGGGCCATT
GTCAGCCCATATATGATGTTGACAGTGATATTGTCGCATGCCA
ATCTGGCAATGCCCATGTGCTCACAGTATGAATGGGGAATTAT
GAGTTTCCCACAATACAGAAGTCGATATACCAGGAAGATGAAT
GGAAAACAGATGAGAAAGCTTCTGACCACAGCTGCTGTGCCA
ATCTTGCCAATGACTGAGGAAGTAAGGATGGTGGTGTATCTTA
GTGGATAACAGATGGCCACATACCTATCCAGCGCCATA

Fig. 7

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (9)..(9)
```

```
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (21)..(21)
<223> OTHER INFORMATION: n stands for inosine

<400> SEQUENCE: 1
atgkcnctng aymgntaygt ngc                                              23

<210> SEQ ID NO 2
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (12)..(12)
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (21)..(21)
<223> OTHER INFORMATION: n stands for inosine
<220> FEATURE:
<221> NAME/KEY: misc_feature
<222> LOCATION: (24)..(24)
<223> OTHER INFORMATION: n stands for inosine
<220> FEATURE:
<221> NAME/KEY: misc_feature
<222> LOCATION: (27)..(27)
<223> OTHER INFORMATION: n stands for inosine

<400> SEQUENCE: 2
tgyttngtyy tnacncyrta natnatnggr tt                                    32

<210> SEQ ID NO 3
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n stands for inosin
<220> FEATURE:
<221> NAME/KEY: misc_feature
<222> LOCATION: (12)..(12)
<223> OTHER INFORMATION: n stands for inosin
<220> FEATURE:
<221> NAME/KEY: misc_feature
<222> LOCATION: (18)..(18)
<223> OTHER INFORMATION: n stands for inosin
<220> FEATURE:
<221> NAME/KEY: misc_feature
<222> LOCATION: (21)..(21)
<223> OTHER INFORMATION: n stands for inosin
<220> FEATURE:
<221> NAME/KEY: misc_feature
<222> LOCATION: (24)..(24)
<223> OTHER INFORMATION: n stands for inosin

<400> SEQUENCE: 3
```

```
gcntaygayc gntaygtngc natntg                                                26
```

```
<210> SEQ ID NO 4
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9)..(9)
<223> OTHER INFORMATION: n stands for inosine
<220> FEATURE:
<221> NAME/KEY: misc_feature
<222> LOCATION: (12)..(12)
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (21)..(21)
<223> OTHER INFORMATION: n stands for inosine
<220> FEATURE:
<221> NAME/KEY: misc_feature
<222> LOCATION: (24)..(24)
<223> OTHER INFORMATION: n stands for inosine
<220> FEATURE:
<221> NAME/KEY: misc_feature
<222> LOCATION: (27)..(27)
<223> OTHER INFORMATION: n stands for inosine

<400> SEQUENCE: 4
tcyttrttnc knagngwrta naynasnggr tt                                          32

<210> SEQ ID NO 5
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n stands for inosine
<220> FEATURE:
<221> NAME/KEY: misc_feature
<222> LOCATION: (9)..(9)
<223> OTHER INFORMATION: n stands for inosine
<220> FEATURE:
<221> NAME/KEY: misc_feature
<222> LOCATION: (12)..(12)
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (21)..(21)
<223> OTHER INFORMATION: n stands for inosine
<220> FEATURE:
<221> NAME/KEY: misc_feature
<222> LOCATION: (24)..(24)
<223> OTHER INFORMATION: n stands for inosine
<220> FEATURE:
<221> NAME/KEY: misc_feature
<222> LOCATION: (27)..(27)
<223> OTHER INFORMATION: n stands for inosine

<400> SEQUENCE: 5
tcntsrttnc knarnsarta natnatnggr tt                                          32
```

```
<210> SEQ ID NO 6
<211> LENGTH: 27
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (4)..(4)
<223> OTHER INFORMATION: n stands for inosine
<220> FEATURE:
<221> NAME/KEY: misc_feature
<222> LOCATION: (7)..(7)
<223> OTHER INFORMATION: n stands for inosine
<220> FEATURE:
<221> NAME/KEY: misc_feature
<222> LOCATION: (10)..(10)
<223> OTHER INFORMATION: n stands for inosine
<220> FEATURE:
<221> NAME/KEY: misc_feature
<222> LOCATION: (16)..(16)
<223> OTHER INFORMATION: n stands for inosine
<220> FEATURE:
<221> NAME/KEY: misc_feature
<222> LOCATION: (22)..(22)
<223> OTHER INFORMATION: n stands for inosine

<400> SEQUENCE: 6
rttncknarn swrtanatra anggrtt                                           27

<210> SEQ ID NO 7
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (21)..(21)
<223> OTHER INFORMATION: n stands for inosine

<400> SEQUENCE: 7
atggcntayg aymgntaygt ngc                                               23

<210> SEQ ID NO 8
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (12)..(12)
<223> OTHER INFORMATION: n stands for inosine
<220> FEATURE:
<221> NAME/KEY: misc_feature
<222> LOCATION: (18)..(18)
<223> OTHER INFORMATION: n stands for inosine

<400> SEQUENCE: 8
atraanggrt tnarcatngg                                                   20
```

```
<210> SEQ ID NO 9
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n stands for inosine
<220> FEATURE:
<221> NAME/KEY: misc_feature
<222> LOCATION: (6)..(6)
<223> OTHER INFORMATION: n stands for inosine
<220> FEATURE:
<221> NAME/KEY: misc_feature
<222> LOCATION: (9)..(9)
<223> OTHER INFORMATION: n stands for inosine
<220> FEATURE:
<221> NAME/KEY: misc_feature
<222> LOCATION: (15)..(15)
<223> OTHER INFORMATION: n stands for inosine
<220> FEATURE:
<221> NAME/KEY: misc_feature
<222> LOCATION: (18)..(18)
<223> OTHER INFORMATION: n stands for inosine
<220> FEATURE:
<221> NAME/KEY: misc_feature
<222> LOCATION: (24)..(24)
<223> OTHER INFORMATION: n stands for inosine

<400> SEQUENCE: 9
acnacngana grtgngansc rcangt                                          26

<210> SEQ ID NO 10
<211> LENGTH: 547
<212> TYPE: DNA
<213> ORGANISM: Artificial
<220> FEATURE:
<223> OTHER INFORMATION: Gene sequence coding for the olfactory receptor
      Olfr67

<400> SEQUENCE: 10
ttgcttggtc ttgacgccat agatgatggg gttaagcatt gggggcacca ccacatagag      60
gttggccact aggatgtgga tgtggcgagg aactgttttg cctccaaagc gatgggcaaa     120
aaatgaaaag aatgcaggag tgtagaataa agaataaca cagatgtggg agccacatgt      180
gttgagggcc ttgtatctgg cagcccagga agggatttga aaaacagtgc gaagaatcat     240
ggtgtaggaa ataatgatga gtagtatatc tagcctagta gacaggaggg ccattgtcag     300
cccatatatg atgttgacag tgatattgtc gcatgccaat ctggcaatgc ccatgtgctc     360
acagtatgaa tggggaatta tgagtttccc acaatacaga agtcgatata ccaggaagat     420
gaatggaaaa cagatgagaa agcttctgac cacagctgct gtgccaatct tgccaatgac     480
tgaggaagta aggatggtgg tgtatcttag tggataacag atggccacat acctatccag     540
cgccata                                                              547
```

METHOD FOR IDENTIFYING OLFACTORY RECEPTOR INCLUDED IN ONE OLFACTORY CELL

INCORPORATION BY REFERENCE

Sequence Listing

The material contained in the ASCII text file named "P634282-02_SEQUENCE_LIST.txt" created on Feb. 7, 2013 and having a file size of 6260 bytes is incorporated by reference herein.

BACKGROUND OF THE INVENTION

1. Field of the Invention

The present invention relates to a method for identifying an olfactory receptor contained in one olfactory cell.

2. Background of the Related Art

An olfactory receptor is a trimeric G protein-coupled receptor (hereinafter, referred to as "GPCR"). More particularly, the olfactory receptor is one kind of trimeric G protein-coupled seven-transmembrane receptors.

FIG. 4 shows a mechanism that a stimulus of an odor molecule to a cell membrane is converted into an electric signal.

The olfactory receptor is a membrane protein which is expressed on the cell membrane. The cell membrane is mainly composed of a lipid bilayer membrane. The lipid bilayer membrane has a structure of two layers each consisting of phospholipid molecules lined with a high density. This lipid bilayer membrane is shown in the center of FIG. 4 schematically. In FIG. 4, the outside of the cell is above the upper part of the lipid bilayer membrane. On the other hand, the inside of the cell is below the lower part of the lipid bilayer membrane. The trimeric G protein is placed in the vicinity of the olfactory receptor.

The trimeric G protein is a heterotrimer composed of an alpha subunit (Gαolf), a beta-subunit (Gβ), and a gamma subunit (Gγ). The cell contains adenylate cyclase. In FIG. 4, the adenylate cyclase is referred to as "AC". To be more exact, the adenylate cyclase is a transmembrane-type protein. A protein RTP1S has a function to assist the olfactory receptors to be expressed in the cell membrane. It is noted that the protein RTP1S is not directly associated with the mechanism.

Next, the mechanism is described. The odor molecule binds to the olfactory receptor. The binding separates the trimeric G protein into the alpha subunit (Gαolf) and a beta-gamma complex. The beta-gamma complex consists of the subunit Gβ and the subunit Gγ. The separated Gαolf activates the adenylate cyclase (AC). The activated adenylate cyclase (AC) converts adenosine triphosphate (ATP) into cyclic adenosine monophosphate (cAMP).

The cyclic adenosine monophosphate (cAMP) activates an ion channel, more particularly, for example, a cyclic nucleotide gated ion channel (CNG). The activation allows an ion to be transported from the inside of the cell to the outside of the cell, or from the outside of the cell to the inside of the cell. The degree of the transport of the ion can be measured as an electric signal.

The mouse contains approximately 1,300 kinds of the olfactory receptors. The olfactory receptor is referred to as "Olfr_n". Generally, n represents a natural number. For example, an olfactory receptor having a name of "Olfr67" is known.

One olfactory cell includes one kind of the olfactory receptor. One olfactory cell does not include two or more kinds of the olfactory receptors.

When an olfactory receptor is not expressed in a cell transfected with a gene sequence coding for an olfactory receptor, a skilled person who has acquired one olfactory cell is not able to identify the olfactory receptor included in the one olfactory cell.

In order to solve this problem, Non Patent Literature 1 discloses a method for identifying an olfactory receptor included in one olfactory cell among Olfr 480, Olfr 544, Olfr 545, Olfr 586, Olfr 642, Olfr 661, Olfr 672, Olfr 690, Olfr 744 and Olfr 749, using a pair of primers represented by SEQ ID: 03 and SEQ ID: 04, a pair of primers represented by SEQ ID: 03 and SEQ ID: 05, or a pair of primers represented by SEQ ID: 03 and SEQ ID: 06.

Non Patent Literature 2 discloses a method for determining whether or not an olfactory receptor included in one olfactory cell is Olfr 16, using a pair of primers represented by SEQ ID: 07 and SEQ ID: 08.

Non Patent Literature 3 discloses a method for identifying an olfactory receptor included in one olfactory cell among Olfr 1056, Olfr 1366 and Olfr 1484, using a pair of primers represented by SEQ ID: 03 and SEQ ID: 09.

CITATION LIST

[Non Patent Literature]
[Non Patent Literature 1]
Bettina Malnic, Junzo Hirono, Takaaki Sato, B. Buck, (1999) Cell, 96, 713-723
[Non Patent Literature 2]
Touhara K., Sengoku S., Inaki K., Tsuboi A., Hirono J., Sato T., Sakano H., Haga T. (1999) Proc. Natl. Acad. Sci., 96, 4040
[Non Patent Literature 3]
Hamana H., Hirono J., Kizumi M., Sato T., Chem. Senses (2003) 28 (2): 87-104.

SUMMARY OF THE INVENTION

Technical Problem

The purpose of the present invention is to provide a novel method for identifying an olfactory receptor included in one olfactory cell.

Solution to Problem

The present invention is a method for identifying an olfactory receptor included in one olfactory cell among a mouse olfactory receptor group A; the method comprising steps of:

(a) obtaining the one olfactory cell;

(b) extracting mRNA contained in the one olfactory cell obtained in the step (a);

(c) obtaining cDNA with reverse transcriptase from the mRNA extracted in the step (b);

(d) amplifying the cDNA obtained in the step (c) by a PCR method using a forward primer represented by SEQ ID: 01 and a reverse primer represented by SEQ ID: 02; wherein SEQ ID:01 is A (adenine) -T (thymine) -G (guanine) -K (guanine or thymine) -C (cytosine) -I (inosine) -C (cytosine) -T (thymine) -I (inosine) -G (guanine) -A (adenine) -Y (thymine or cytosine) -M (adenine or cytosine) -G (guanine) -I (inosine) -T (thymine) -A (adenine) -Y (thymine or cytosine) -G (guanine) -T (thymine) -I (inosine) -G (guanine) -C (cytosine); and SEQ ID: 02 is T (thymine) -G (guanine) -Y (thymine or cytosine) -T (thymine) -T (thymine) -I (inosine) -G (guanine) -T (thymine) -Y (thymine or cytosine) -Y (thymine or cytosine) -T (thymine) -I (inosine) -A (adenine) -C (cytosine) -I (inosine) -C (cytosine) -Y (thymine or cytosine) -R (guanine or adenine) -T (thymine) -A (adenine) -I (inosine) -A (adenine) -T (thymine) -I (inosine) -A (adenine) -T (thymine) -I (inosine) -G (guanine) -G (guanine) -R (guanine or adenine) -T (thymine) -T (thymine);

(e) determining whether or not a gene sequence of the cDNA amplified in the step (d) is identical to one gene sequence included in gene sequences coding for olfactory receptors included in the mouse olfactory receptor group A;

(f) determining that, if the gene sequence of the cDNA is identical to the one gene sequence in the step (e), the olfactory receptor included in the one olfactory cell is the olfactory receptor which corresponds to the one gene sequence which is identical the gene sequence of the cDNA in the step (e);

where the mouse olfactory receptor group A includes the following mouse olfactory receptors:

(Mouse Olfactory Receptor Group A)

Olfr17, Olfr64, Olfr67, Olfr68, Olfr155, Olfr168, Olfr510, Olfr544, Olfr545, Olfr548-ps1, Olfr551, Olfr560, Olfr566, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, Olfr1101, and Olfr1402.

In one embodiment, a cell membrane of the one olfactory cell between the step (a) and the step (b) is disrupted.

In one embodiment, the one olfactory cell is extracted from a sample solution containing olfactory cells in the step (a).

In one embodiment, the mouse olfactory receptor group A is selected from the following mouse olfactory receptor group B:

(Mouse Olfactory Receptor Group B)

Olfr 17, Olfr 64, Olfr 67, Olfr 68, Olfr168, Olfr510, Olfr548-ps1, Olfr551, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, and Olfr1101.

Advantageous Effects of Invention

The present invention provides a novel method for identifying an olfactory receptor included in one olfactory cell.

BRIEF DESCRIPTION OF DRAWINGS

FIG. 5 shows SEQ ID: 03-SEQ ID: 06.

FIG. 6 shows SEQ ID: 07-SEQ ID: 09.

FIG. 7 shows SEQ ID: 10.

DETAILED DESCRIPTION OF THE INVENTION

Figure 1:
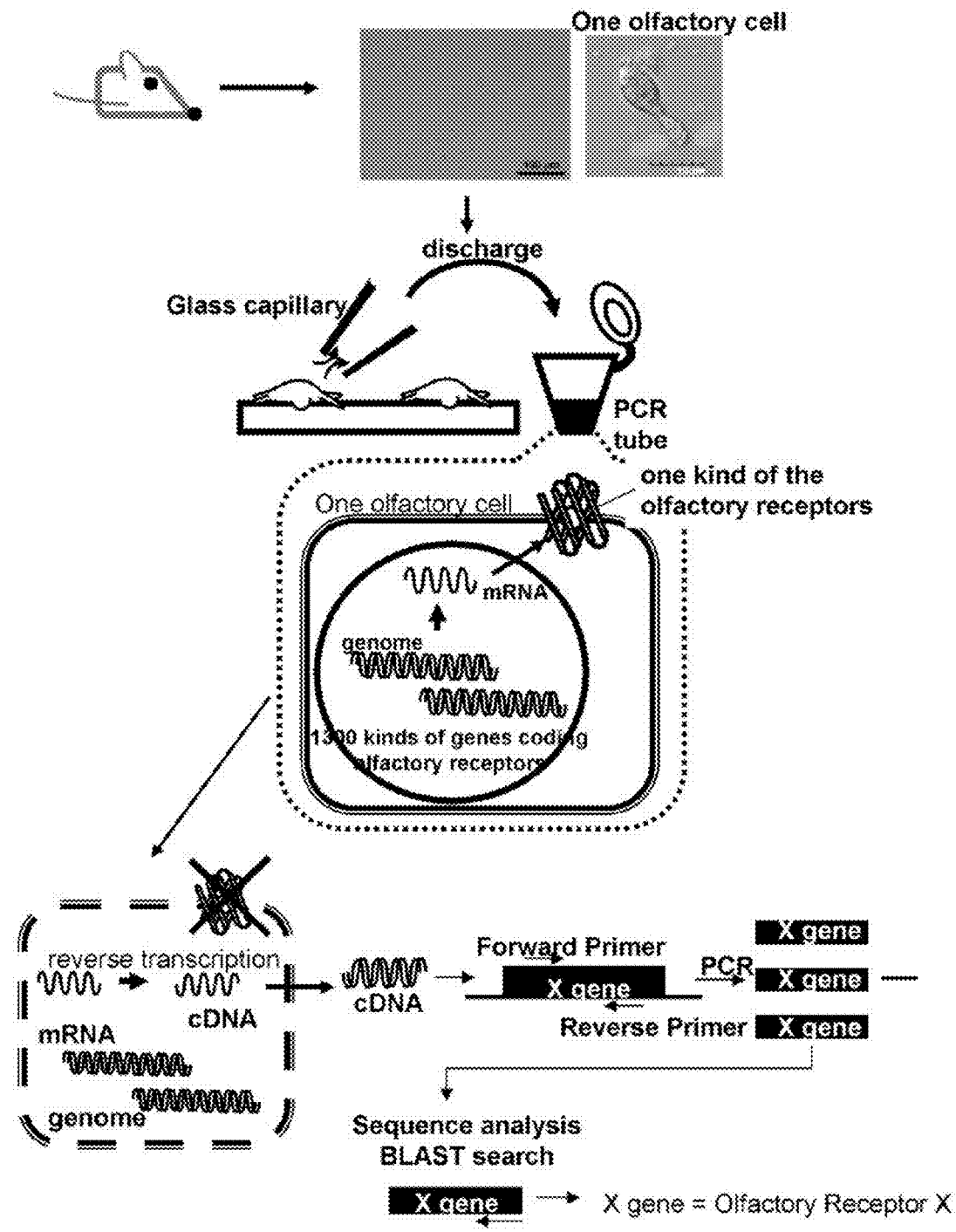
FIG. 1 shows a schematic diagram of the example 1.

The embodiment of the present invention is described below.

(Definition of Term)

The term "mouse olfactory receptor group A" used in the instant specification means mouse olfactory receptors Olfr17, Olfr64, Olfr67, Olfr68, Olfr155, Olfr168, Olfr510, Olfr544, Olfr545, Olfr548-ps1, Olfr551, Olfr560, Olfr566, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, Olfr1101, and Olfr1402.

The term "mouse olfactory receptor group B" used in the instant specification means mouse olfactory receptors Olfr 17, Olfr 64, Olfr 67, Olfr 68, Olfr168, Olfr510, Olfr548-ps1, Olfr551, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, and Olfr1101.

In the instant specification, "Olfr" having "O" of a capital letter means an olfactory receptor.

In the instant specification, "olfr" having "o" of a small letter means a gene sequence coding for an olfactory receptor.

A skilled person who has read the instant specification could identify an olfactory receptor included in one olfactory cell among the mouse olfactory receptor group A. Unfortunately, a skilled person could NOT identify an olfactory receptor, when the olfactory receptor included in one olfactory cell is NOT an olfactory receptor included in the mouse olfactory receptor group A (For example, when the olfactory receptor is Olfr 2).

Generally, an olfactory receptor is included in one olfactory cell in such a manner that the olfactory receptor penetrates a cell membrane of the one olfactory cell.

(Step (a))

First, one olfactory cell is prepared. It is desirable that the one olfactory cell is extracted from a sample solution containing olfactory cells. More particularly, the sample solution is supplied onto a petri dish. One olfactory cell contained in the sample solution which has been supplied onto the petri dish is found with a microscope. The one olfactory cell thus found is collected into a capillary tube. In this way, the one olfactory cell is isolated. The one olfactory cell is derived from a mouse.

(Step (b))

In the step (b), mRNA contained in the one olfactory cell obtained in the step (a) is extracted. More particularly, the cell membrane of the one olfactory cell is disrupted with a cell lysate to extract the mRNA contained in the one olfactory cell. The cell lysate is included in a kit available from Takara bio Co., Ltd., as a commercial name: CellAmp Whole Transcriptome Amplification Kit Ver2.

(Step (c))

In the step (c), cDNA is obtained with reverse transcriptase from the mRNA extracted in the step (b). To obtain the cDNA using the reverse transcriptase from the mRNA, used is a kit available from Takara bio Co., Ltd., as a commercial name: CellAmp Whole Transcriptome Amplification Kit Ver2.

(Step (d))

In the step (d), the cDNA obtained in the step (c) is amplified by a PCR method using a forward primer represented by SEQ ID: 01 and a reverse primer represented by SEQ ID: 02.

SEQ ID:01 is A (adenine) -T (thymine) -G (guanine) -K (guanine or thymine) -C (cytosine) -I (inosine) -C (cytosine) -T (thymine) -I (inosine) -G (guanine) -A (adenine) -Y (thymine or cytosine) -M (adenine or cytosine) -G (guanine) -I (inosine) -T (thymine) -A (adenine) -Y (thymine or cytosine) -G (guanine) -T (thymine) -I (inosine) -G (guanine) -C (cytosine).

SEQ ID: 02 is T (thymine) -G (guanine) -Y (thymine or cytosine) -T (thymine) -T (thymine) -I (inosine) -G (guanine) -T (thymine) -Y (thymine or cytosine) -Y (thymine or cytosine) -T (thymine) -I (inosine) -A (adenine) -C (cytosine) -I (inosine) -C (cytosine) -Y (thymine or cytosine) -R (guanine or adenine) -T (thymine) -A (adenine) -I (inosine) -A (adenine) -T (thymine) -I (inosine) -A (adenine) -T (thymine) -I (inosine) -G (guanine) -G (guanine) -R (guanine or adenine) -T (thymine) -T (thymine).

When the olfactory receptor included in the one olfactory cell is an olfactory receptor included in the mouse olfactory receptor group A, the cDNA is amplified in the step (d) by a PCR method. On the other hand, when the olfactory receptor included in the one olfactory cell is NOT an olfactory receptor included in the mouse olfactory receptor group A, the cDNA is NOT amplified in the step (d) by a PCR method. If the cDNA is amplified in the step (d), the next step (e) is carried out.

(Step (e))

In the step (e), it is determined whether or not the gene sequence of the cDNA amplified in the step (d) is identical to one gene sequence included in gene sequences coding for the olfactory receptors included in the mouse olfactory receptor group A.

More particularly, the gene sequence of the cDNA amplified in the step (d) is analyzed. Then, one gene sequence which is identical to the analyzed gene sequence is found by a BLAST search method from among a plurality of known gene sequences olfrs which are coding for olfactory receptors Olfrs. Regarding the 20 BLAST search method, refer to the following home page: blast.ncbi.nlm.nih.gov/Blast.cgi. In addition, the gene sequence coding for each of the olfactory receptors included in the mouse olfactory receptor group A is known.

For example, when the gene sequence of the cDNA amplified in the step (d) corresponds with the gene sequence olfr 67 by the BLAST search method, it is determined that the olfactory receptor included in the one olfactory cell is Olfr 67.

(Step (f))

In this way, in the step (e), when the gene sequence of the cDNA is identical to one gene sequence included in the gene sequences coding for the olfactory receptors included in the mouse olfactory receptor group A, it is determined that the olfactory receptor included in the one olfactory cell is the olfactory receptor corresponding to the one gene sequence which is identical to the gene sequence of the cDNA in the step (e).

EXAMPLE

The following examples describe the present invention in more detail.

(Preparation of the Sample Solution Containing Olfactory Cells)

One mouse C57/BL6J (female) was purchased from Japan SLC, Inc. The mouse was 3-5 weeks old.

An anesthetic agent (pentobarbital sodium, 100 microliters, available from Kyoritsu Seiyaku Corporation) diluted tenfold with a saline (available from Otsuka Pharmaceutical Co., Ltd.) was injected into the abdominal cavity of the mouse using an injector having a needle of 1 milliliter. The mouse was left at rest for five minutes.

After it was confirmed that the mouse was in the anesthetic state, the mouse head was cut off with scissors.

In order to prevent the mouse tissue from being necrotized, the mouse head was immediately immersed in a sherbet of a $Ca^{2+}$-free Ringer's solution prepared in a beaker having a volume of 50 milliliters. The mouse head was immersed in the sherbet for five minutes.

The $Ca^{2+}$-free Ringer's solution had a composition shown in the following Table 1.

TABLE 1

| Chemical reagent | Concentration |
|---|---|
| NaCl | 140 mM |
| KCl | 5 mM |
| HEPES | 10 mM |
| EDTA | 1 mM |
| Glucose | 10 mM |
| Pyruvate sodium | 1 mM |

These chemical reagents contained in the $Ca^{2+}$-free Ringer's solution were obtained from Wako Pure Chemical Industries, Ltd. The $Ca^{2+}$-free Ringer's solution had a pH of 7.2.

The mouse head thus cooled was moved to a sherbet of a $Ca^{2+}$-free Ringer's solution prepared in a deep petri dish. Subsequently, while the mouse head was cooled, an olfactory epithelium tissue included in the mouse head was isolated.

The isolated olfactory epithelium tissue was dispersed in a $Ca^{2+}$-free Ringer's solution cooled on ice. This $Ca^{2+}$-free Ringer's solution had not only the chemical reagents shown in the following Table 1 but also the chemical reagents shown in the following Table 2. In this way, an olfactory epithelium sample solution was obtained.

TABLE 2

| Chemical reagent | Concentration | Available from |
|---|---|---|
| Papain | 1 unit/milliliter | Sigma Aldrich |
| Cystein | 1 mM | Wako Pure Chemical Industries, Ltd. |

Then, the olfactory epithelium sample solution was stirred calmly under a room temperature with a rotator (available from AS ONE Corporation, commercial name: MTR-103). During this stir, decomposition reaction of protein was proceeded by the papain, which is a proteolytic enzyme.

Five minutes later, a Ringer's solution (1,600 microliters) containing the chemical reagents shown in Table 3 was added to the olfactory epithelium sample solution to stop the enzyme reaction of the papain.

TABLE 3

| Chemical reagent | Concentration | Available from |
|---|---|---|
| Leupeptin | 500 µM | Sigma Aldrich |
| Dnase I | 200 unit/milliliter | Worthington Biochemical Co. |
| BSA | 0.1 mg/mL | Sigma Aldrich |
| NaCl | 140 mM | Wako Pure Chemical Industries, Ltd. |
| KCl | 5 mM | |
| $CaCl_2$ | 1 mM | |
| $MgCl_2$ | 1 mM | |
| HEPES | 10 mM | |
| Glucose | 10 mM | |
| Pyruvate sodium | 1 mM | |

The $Ca^{2+}$-free Ringer's solution had a pH of 7.2.

The olfactory epithelium sample solution was passed twice through a cell strainer (available from BD Falcon company, 35 micrometers mesh). In this way, large tissue fragments were removed to obtain an olfactory cell suspension.

The obtained olfactory cell suspension was subjected to a centrifugal separation at an rpm (revolutions per minutes) of 1000 for five minutes. After the supernatant liquid was removed, three milliliters of the Ringer's solution was newly added. In this way, an olfactory cell sample solution was prepared.

(Step (a): Isolation of One Olfactory Cell)

The olfactory cell sample solution was supplied to a culture petri dish (available from BD falcon company) having a diameter of 60 millimeters. Subsequently, the olfactory cell sample solution was left at rest under a temperature of 37 degrees Celsius for 30 minutes. In this way, the olfactory cell was adsorbed on the culture petri dish.

One olfactory cell was collected from this culture petri dish with a microscope (available from Olympus Corporation, a commercial name: IX-81). In more detail, a glass tube (available from Sutter Instruments Co., commercial name: B150-86-10) was steepled with a capillary tube puller (available from Sutter Instruments Co., commercial name: P-97/IVF). The sharpened end of this glass tube had a diameter of 10 micrometers.

Then, the Ringer's solution having the composition shown in Table 4 was filled by capillarity phenomenon into the sharpened end of the glass tube.

TABLE 4

| Chemical reagent name | Concentration | Available from |
| --- | --- | --- |
| NaCl | 140 mM | Wako Pure Chemical Industries, Ltd. |
| KCl | 5 mM | |
| $CaCl_2$ | 1 mM | |
| $MgCl_2$ | 1 mM | |
| HEPES | 10 mM | |
| Glucose | 10 mM | |
| Pyruvate sodium | 1 mM | |

The glass tube was installed with a microinjector (available from Eppendorf company, commercial name: CellTram vario) which was connected to a manipulator (available from Narishige Co., Ltd., commercial name: MMN-1). After the one olfactory cell absorbed on the culture petri dish was found with the microscope, the sharpened end of the glass tube was set manually in the neighborhood of the one olfactory cell, using the manipulator. Subsequently, the one olfactory cell was collected into the glass tube with a microinjector by capillarity phenomenon.

(Step (b): Extraction of mRNA)

mRNA was extracted from the collected one olfactory cell. This extraction was carried out using a kit available from Takara Bio Inc. as a commercial name "CellAmp Whole Transcriptome Amplification Kit Ver2". This kit was also used in the next step (c).

In more detail, the collected one olfactory cell was discharged into the PCR tube containing cell lysate (4.5 microliters) which was attached in the kit. The PCR tube was left under a temperature of 70 degrees Celsius for 90 seconds. In this way, the mRNA was obtained in the PCR tube.

(Step (c): Synthesis of cDNA)

According to the manual attached to the kit, cDNA was synthesized from the mRNA obtained in the step (b). In this way, an aqueous solution (25 microliters) which contained the cDNA was obtained. Pure water of 225 microliter was added to this aqueous solution.

(Step (d): Amplification of the cDNA)

PCR was performed using the cDNA obtained in the step (c), a forward primer represented by SEQ ID: 01, and a reverse primer represented by SEQ ID: 02.

Table 5 shows the composition of the solution used in this PCR.

TABLE 5

| | Volume (Unit: microliter) | Concentration |
| --- | --- | --- |
| 2x GC buffer I (attached in the kit) | 12.5 | — |
| dNTPs (available from Takara bio inc.) | 4 | 0.4 mM |
| Forward primer | 1 | 1.2 µM |
| Reverse primer | 1 | 1.2 µM |
| cDNA template | 2.5 | — |
| Pure water | 3.75 | |
| Takara LA Taq | 0.25 | |
| Total | 25 | |

Table 6 shows the protocol of this PCR.

TABLE 6

| Step | Temperature | Time |
| --- | --- | --- |
| 1 | 94 degrees Celsius | 1 minute |
| 2 | 94 degrees Celsius | 30 seconds |
| 3 | 40 degrees Celsius | 30 seconds |
| 4 | 72 degrees Celsius | 2 minutes |
| 5 | After the steps 2-4 were repeated 40 times, the step 6 were performed. | |
| 6 | 72 degrees Celsius | 5 minutes |
| 7 | 4 degrees Celsius | 18 hours |

After the PCR, a part of the PCR solution was subjected to electrophoresis using an agarose gel. In this way, it was confirmed that a part of the gene coding for an olfactory receptor was amplified.

(Step (e))

The other part of the PCR solution was subjected to electrophoresis using another agarose gel. Subsequently, the agarose gel was irradiated with ultra-violet rays to obtain plural bands derived from the PCR products. Then, a part of the agarose gel which contained each band was isolated. The gene segment contained in the isolated agarose gel was purified with a filter column (available from GL science, commercial name: MonoFas DNA purification kit). The forward primer represented by SEQ ID: 01 was added to the purified gene segment. Then, the gene sequence of the gene segment was analyzed. As a result, it was found that the gene segment consisted of the gene sequence represented by SEQ ID: 10.

The BLAST search method was used to identify the gene sequence represented by SEQ ID: 10. For more detail of the BLAST search method, see the following home page: blast.ncbi.nlm.nih.gov/Blast.cgi.

As a result, the gene sequence represented by SEQ ID: 10 was identical to the gene sequence olfr 67.

(Step (f))

Therefore, the olfactory receptor included in the one olfactory cell obtained in a step (a) was identified as the olfactory receptor Olfr 67.

Comparative Example 1

The experiment similar to the example 1 was conducted, except that a pair of primers represented by SEQ ID: 03 and SEQ ID: 04 were used instead of the pair of the primers represented by SEQ ID: 01 and SEQ ID: 02.

Comparative Example 2

The experiment similar to the example 1 was conducted, except that a pair of primers represented by SEQ ID: 05 and SEQ ID: 07 were used instead of the pair of the primers represented by SEQ ID: 01 and SEQ ID: 02.

Comparative Example 3

The experiment similar to the example 1 was conducted, except that a pair of primers represented by SEQ ID: 06 and SEQ ID: 07 were used instead of the pair of the primers represented by SEQ ID: 01 and SEQ ID: 02.

Figure 2:
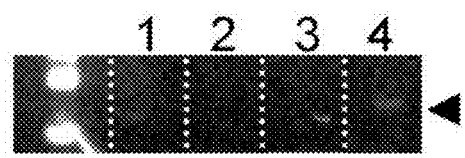
FIG. 2 shows an electrophoretic photograph according to the comparative example 1, the comparative example 2, the comparative example 3, and the example 1.
Figure 3:
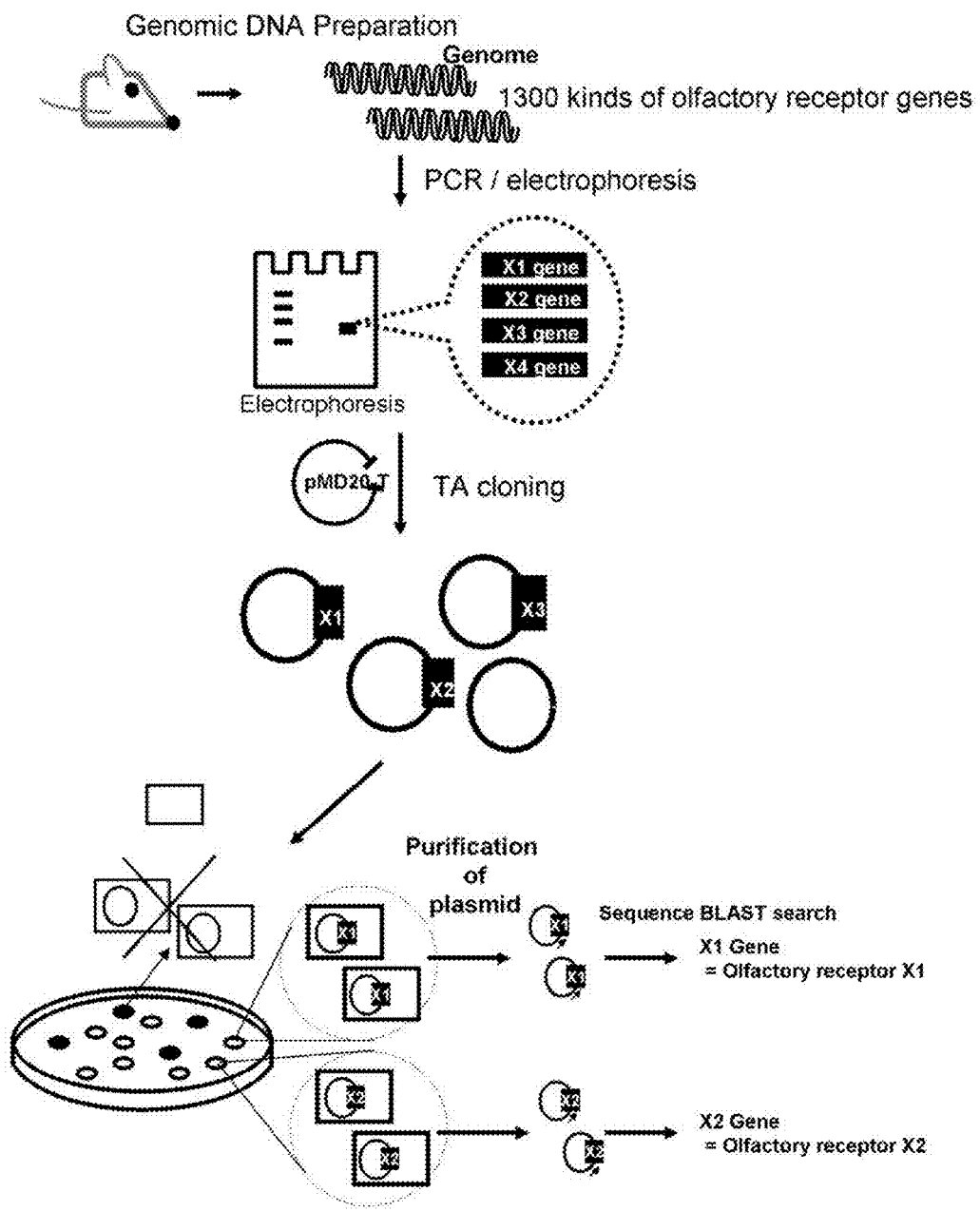
FIG. 3 shows a schematic diagram of the reference example.
Figure 4:
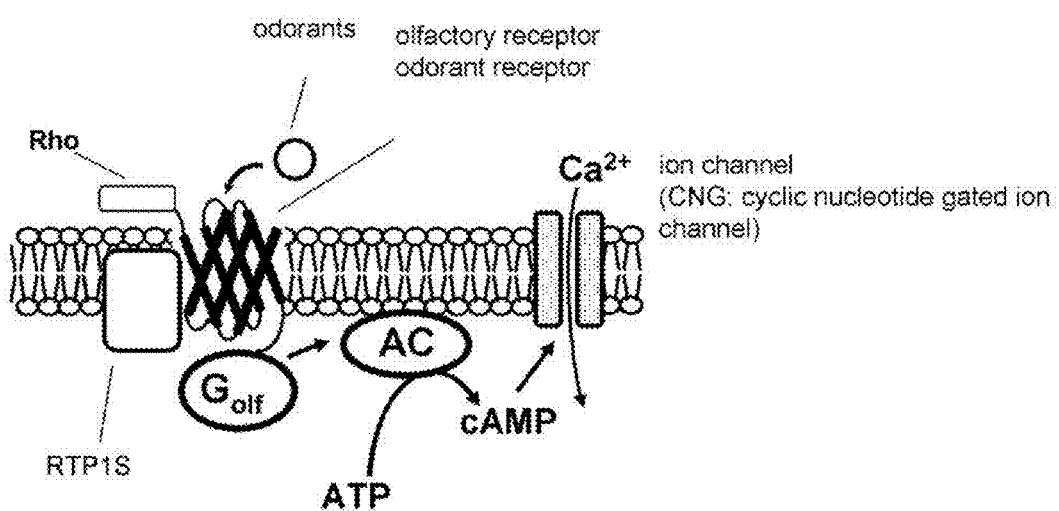
FIG. 4 shows a mechanism that a stimulus of an odor molecule to a cell membrane is converted into an electric signal.

FIG. 2 shows an electrophoretic photograph in the neighborhood of 600 base pairs in the comparative example 1, the comparative example 2, the comparative example 3, and the example 1.

In FIG. 2, the column 1, the column 2, the column 3, and the column 4 correspond to the comparative example 1, the comparative example 2, the comparative example 3, and the example 1, respectively. The column 0 in FIG. 2 corresponds to a molecular weight marker.

As shown in FIG. 2, a band was observed in the neighborhood of 600 base pairs only in the example 1. This means that only the pair of the primers represented by SEQ ID: 01 and SEQ ID: 02 achieve the amplification of the gene sequence olfr 67.

Reference Example 1

The following reference example 1 was performed to determine which the olfactory receptor genes olfrs are amplified with the pair of the primers represented by SEQ ID: 01 and SEQ ID: 02.

To start with the conclusion, the olfactory receptor genes olfrs which can be amplified by a PCR method using the pair of the primers represented by SEQ ID: 01 and SEQ ID: 02 are listed in the following Table 7 as "Olfactory receptor gene group A".

TABLE 7

| (Olfactory receptor gene group A) |
| --- |
| Olfr17, Olfr64, Olfr67, Olfr68, Olfr155, Olfr168, Olfr510, Olfr544, Olfr545, Olfr548-ps1, Olfr551, Olfr560, Olfr566, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, Olfr1101, and Olfr1402 |
| (Total: thirty seven kinds) |

The olfactory receptor genes olfrs listed in Table 7 corresponds to the olfactory receptors Olfrs of the mouse olfactory receptor group A.

(Preparation of the Mouse Genomic DNA)

One mouse C57/BL6J (female) was purchased from Japan SLC, Inc. The mouse was 3-5 weeks old. The mouse tail was cut. The cut mouse tail had a length of approximately 1 millimeter.

A mouse genomic DNA was prepared using a kit (available from Qiagen company, commercial name: DNeasy Blood & Tissue Kit) from the separated mouse.

A PCR was performed using this mouse genomic DNA, the forward primer represented by SEQ ID: 01, and the reverse primer represented by SEQ ID: 02.

The DNA polymerase used in this PCR was obtained from Takara bio inc. as a commercial name "LA-Taq with GC Buffer".

A PCR solution similar to the PCR solution shown in Table 5 was prepared, except that the mouse genomic DNA having a concentration of 5 nanograms/microliter was added instead of the template cDNA. This solution was used in the above-mentioned PCR.

The protocol used in the PCR was identical to the protocol shown in Table 6.

In this way, PCR products were obtained.

A part of the obtained PCR products was subjected to electrophoresis using an agarose gel.

After the electrophoresis, the agarose gel was irradiated with ultra-violet rays to find a band derived from the PCR products. Subsequently, a part of the agarose gel including the band was isolated.

The PCR product contained in the part of the isolated agarose gel was purified with a filter column (available from GL science company, commercial name: MonoFas DNA purification kit).

The purified PCR products were composed of various types of gene segments. In order to determine the gene sequence of each gene segment, these gene segments were inserted into expression plasmids, and a TA cloning was performed with E. coli. The detail of the TA cloning is described below.

A part of the purified PCR products, a plasmid (available from Takara bio inc., commercial name: pMD20-T), and ligase ((available from Takara bio inc., commercial name: DNA ligation kit ver1) were mixed in pure water. After mixing, the mixture was left under a temperature of 16 degrees Celsius for 30 minutes. In this way, prepared were the plasmids where the purified PCR products, namely, the purified gene sequences, were inserted.

An aqueous E. Coli solution (available from Toyobo Co., Ltd., commercial name: DH5α, as E. Coli) was added to the aqueous solution containing these plasmids to obtain a mixture. Subsequently, the mixture was left under a temperature of 4 degrees Celsius for 15 minutes. Furthermore, the mixture was left under a temperature of 42 degrees Celsius for 90 seconds. Finally, the mixture was left under a temperature of 4 degrees Celsius for three minutes. In this way, the E. Coli was transformed with the plasmids.

The E. Coli transformed with the plasmids was incubated under a temperature of 37 degrees Celsius for 15 hours on an LB plate (available from InvivoGen company, commercial name "fas-am-x").

The LB plate had a culture medium containing the composition shown in following Table 8.

TABLE 8

| Chemical reagent | Concentration |
| --- | --- |
| Ampicillin | 100 micrograms/milliliter |
| X-gal | 100 micrograms/milliliter |
| IPTG | 100 micrograms/milliliter |

After the incubation, white colonies formed on the LB plate were collected. The number of the collected colonies was approximately 110. Each colony was incubated under a temperature of 37 degrees Celsius for 15 hours in the LB liquid medium containing ampicillin having a concentration of 100 micrograms/microliter to obtain an *E. Coli* solution.

The plasmids where the gene segments were inserted were purified from the *E. Coli* solution with a plasmid purification kit (available from Qiagen company commercial name: DirectPrep 96 MiniPrep Kit).

A primer (available from Takara bio inc., commercial name: M13) was added to a part of the purified plasmid aqueous solution. Subsequently, the plasmid aqueous solution was commissioned to Greiner Bio-One Co. Ltd. (Japan) to analyze the gene sequence included in the PCR products.

The amplified olfactory receptor genes olfrs were identified by the BLAST search method on the basis of the gene sequence analyzed by Greiner Bio-One Co. Ltd. (Japan). As a result, it was found that the thirty seven kinds of the olfactory receptor genes olfrs shown in Table 7 were amplified.

Reference Comparative Example 1

The experiment similar to the reference example 1 was conducted, except that the pair of the primers represented by SEQ ID: 03 and SEQ ID: 04 were used instead of the pair of the primers represented by SEQ ID: 01 and SEQ ID: 02.

As a result, it was found that forty-seven kinds of the olfactory receptor genes olfrs were amplified. These forty-seven kinds of the olfactory receptor genes olfrs are shown in Table 9 as "Olfactory receptor gene group C1".

TABLE 9

(Olfactory receptor gene group C1)

olfr16, olfr30, olfr53, olfr90, olfr92, olfr132, olfr136, olfr155, olfr159, olfr160, olfr164, olfr287, olfr288, olfr317, olfr333, olfr374, olfr457, olfr483, olfr498, olfr517, olfr535, olfr713, olfr715, olfr764, olfr769, olfr796, olfr944, olfr977-ps1, olfr982, olfr998, olfr1096, olfr1097, olfr1098, olfr1099, olfr1120, olfr1130, olfr1162, olfr1178, olfr1208, olfr1261, olfr1294, olfr1297, olfr1348, olfr1349, olfr1359, olfr1393, and olfr1507

Reference Comparative Example 2

The experiment similar to the reference example 1 was conducted, except that the pair of the primers represented by SEQ ID: 05 and SEQ ID: 07 were used instead of the pair of the primers represented by SEQ ID: 01 and SEQ ID: 02.

As a result, it was found that twenty-six kinds of the olfactory receptor genes olfrs were amplified. These twenty-six kinds of the olfactory receptor genes olfrs are shown in Table 10 as "Olfactory receptor gene group C2".

TABLE 10

(Olfactory receptor gene group C2)

olfr2, olfr6, olfr32, olfr62, olfr119, olfr141, olfr155, olfr159, olfr220, olfr544, olfr545, olfr560, olfr566, olfr1010, olfr1095, olfr1126, olfr1129, olfr1130, olfr1150, olfr1257, olfr1274, olfr1342, olfr1347, olfr1348, olfr1402, and olfr1506

Reference Comparative Example 3

The experiment similar to the reference example 1 was conducted, except that the pair of the primers represented by SEQ ID: 06 and SEQ ID: 07 were used instead of the pair of the primers represented by SEQ ID: 01 and SEQ ID: 02.

As a result, it was found that forty-three kinds of the olfactory receptor genes olfrs were amplified. These forty-three kinds of the olfactory receptor genes olfrs are shown in Table 11 as "Olfactory receptor gene group C3".

TABLE 11

(Olfactory receptor gene group C3)

olfr22, olfr23, olfr24, olfr49, olfr51, olfr62, olfr70, olfr133, olfr136, olfr138, olfr141, olfr228, olfr350, olfr373, olfr374, olfr382, olfr386, olfr389, olfr392, olfr393, olfr395, olfr397, olfr459, olfr483, olfr701, olfr711, olfr790, olfr796, olfr854, olfr860, olfr1126, olfr1129, olfr1155, olfr1328, olfr1338, olfr1342, olfr1355, olfr1424, olfr1425, olfr1491, olfr1496, olfr1507, and olfr1509

The gene sequences olfrs amplified only with the pair of the primers represented by SEQ ID: 01 and SEQ ID: 02 were extracted on the basis of the following formula. Hereinafter, the term "Olfactory receptor gene group B" includes the olfactory genes olfrs amplified only with the pair of the primers represented by SEQ ID: 01 and SEQ ID: 02.

"Olfactory receptor gene group *B*"="Olfactory receptor gene group *A*"−("Olfactory receptor gene group *C*1"+"Olfactory receptor gene group *C*2"+ "Olfactory receptor gene group *C*3")

Needless to say, the olfactory receptor genes olfrs included in the olfactory receptor gene group B fails to be amplified with a pair of primers other than the pair of the primers represented by SEQ ID: 01 and SEQ ID: 02. The olfactory receptor gene group B corresponds to the mouse olfactory receptor group B.

The present invention provides a novel method for identifying an olfactory receptor included in one olfactory cell.

The invention claimed is:
1. A method for identifying an olfactory receptor included in one olfactory cell among mouse olfactory receptor group A, the method comprising the steps of:
(a) obtaining the one olfactory cell;
(b) extracting mRNA contained in the one olfactory cell obtained in step (a);
(c) obtaining cDNA with reverse transcriptase from the mRNA extracted in step (b);
(d) amplifying the cDNA obtained in step (c) by a PCR method using primers of SEQ ID NO: 1 and SEQ ID NO: 2;
wherein SEQ ID NO:1 consists of A (adenine) -T (thymine) -G (guanine) -K (guanine or thymine) -C (cytosine) -I (inosine) -C (cytosine) -T (thymine) -I (inosine) -G (guanine) -A (adenine) -Y (thymine or cytosine) -M (adenine or cytosine) -G (guanine) -I (inosine) -T (thymine) -A (adenine) -Y (thymine or cytosine) -G (guanine) -T (thymine) -I (inosine) -G (guanine) -C (cytosine); and
SEQ ID NO: 2 consists of T (thymine) -G (guanine) -Y (thymine or cytosine) -T (thymine) -T (thymine) -I (inosine) -G (guanine) -T (thymine) -Y (thymine or cytosine) -Y (thymine or cytosine) -T (thymine) -I (inosine) -A (adenine) -C (cytosine) -I (inosine) -C (cytosine) -Y (thymine or cytosine) -R (guanine or adenine) -T (thymine) -A (adenine) -I (inosine) -A (adenine) -T (thymine) -I (inosine) -A (adenine) -T (thymine) -I (inosine) -G (guanine) -G (guanine) -R (guanine or adenine) -T (thymine) -T (thymine); and
(e) determining whether or not the sequence of the cDNA amplified in step (d) is identical to the gene sequences coding for olfactory receptors included in the mouse olfactory receptor group A; wherein the mouse olfactory receptor group A gene sequences include the following mouse olfactory receptors: Olfr17, Olfr64, Olfr67, Olfr68, Olfr155, Olfr168, Olfr510, Olfr544, Olfr545, Olfr548-ps1, Olfr551, Olfr560, Olfr566, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, Olfr1101, and Olfr1402.

2. The method according to claim 1, further comprising disrupting a cell membrane of the one olfactory cell between step (a) and step (b).

3. The method according to claim 1, wherein the one olfactory cell is extracted from a sample solution containing olfactory cells in step (a).

4. The method according to claim 1, wherein the mouse olfactory receptor group A gene sequence is selected from the following Mouse olfactory receptor group B: Olfr17, Olfr64, Olfr67, Olfr68, Olfr168, Olfr510, Olfr548-psl, Olfr551, Olfr568, Olfr569, Olfr578, Olfr582, Olfr583, Olfr584, Olfr585, Olfr606, Olfr611, Olfr617, Olfr619, Olfr625-ps1, Olfr630, Olfr640, Olfr646, Olfr649, Olfr652, Olfr665, Olfr666, Olfr667, Olfr668, Olfr995, and Olfr1101.

* * * * *